United States Patent [19]

Kurz

[11] Patent Number: 4,514,171
[45] Date of Patent: Apr. 30, 1985

[54] ORTHODONTIC TOOL

[76] Inventor: Craven H. Kurz, 465 N. Roxbury Dr., #1011, Beverly Hills, Calif. 90210

[21] Appl. No.: 635,562

[22] Filed: Jul. 30, 1984

[51] Int. Cl.³ ............................................... A61C 7/00
[52] U.S. Cl. ........................................................ 433/4
[58] Field of Search .................... 433/4, 160, 81, 424

[56] References Cited

U.S. PATENT DOCUMENTS 3,986,265 10/1976 Cusato ................................ 433/4
4,248,587 2/1981 Kurz .................................... 433/4

Primary Examiner—Robert Peshock
Attorney, Agent, or Firm—Keith D. Beecher

[57] ABSTRACT

A tool in the form of specially constructed pliers for removing orthodontic appliances which have been adhesively bonded to the lingual surfaces of the anterior and/or posterior teeth for orthodontic treatment. The tool is equipped with a spring-loaded pivoted catch having a tip which fits under the edge of the appliance to be removed, and a head having a depending post which is inserted between the base of the appliance and the surface of the tooth to which the appliance is bonded, and handles are provided respectively connected to the head and tip and which are pivotally coupled to a bracket to turn about respective spaced pivot axes, so that when the handles are squeezed together against a spring-bias the bonded appliance is stripped from the lingual surface of the tooth without any tendency to torque the tooth during the process.

5 Claims, 2 Drawing Figures

U.S. Patent    Apr. 30, 1985    4,514,171
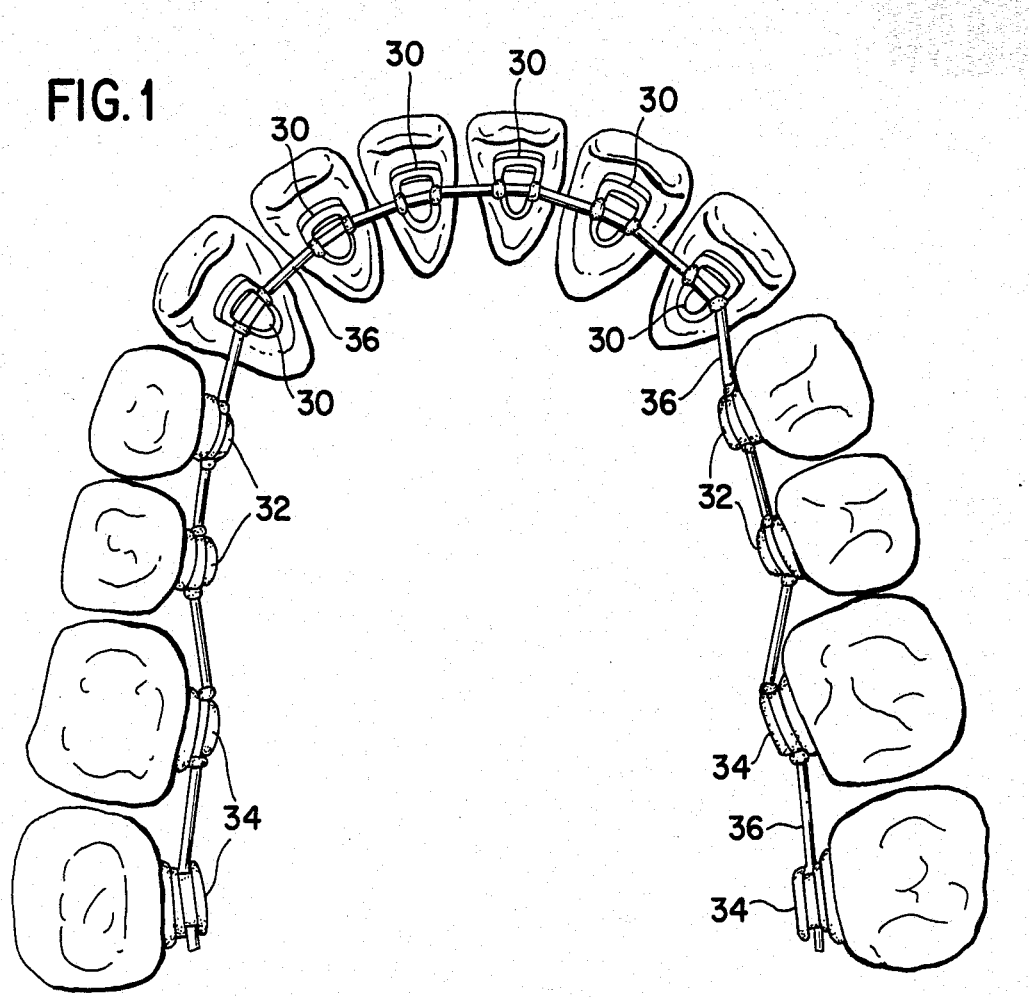
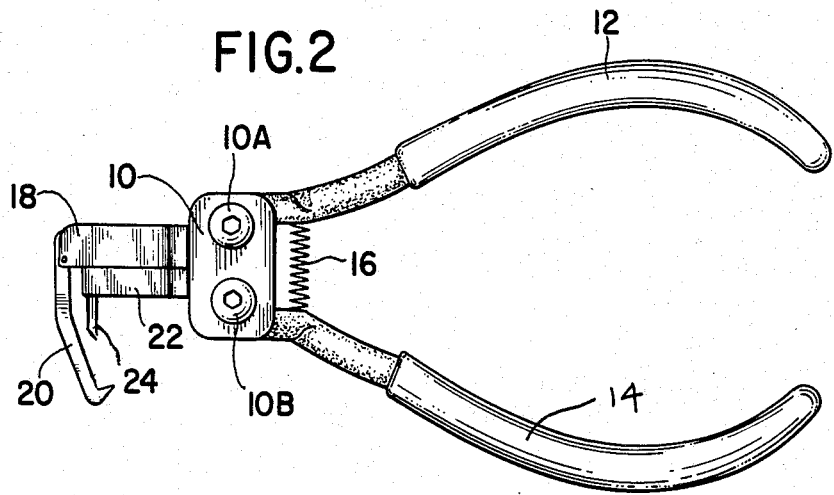

ORTHODONTIC TOOL

BACKGROUND OF THE INVENTION

Copending Application Ser. No. 301,452, filed Sept. 14, 1981, in the name of the present inventor, describes an orthodontic treatment by which brackets and tubes are adhesively bonded to the lingual surfaces of the teeth. Problems arise in effectuating the speedy and easy removal of the adhesively bonded brackets from the lingual surfaces of the teeth after the orthodontic treatment has been completed.

U.S. Pat. No. 4,248,587 which issued Feb. 3, 1981 in the name of the present inventor provides specially constructed pliers which are particularly adapted for removing adhesively bonded brackets and/or tubes from the lingual surfaces of a patient's teeth. The orthodontic tool of the present invention is generally similar to the tool described in the patent. However, the orthodontic tool of the invention provides double-axis pivotal action, and it is sturdier in its construction and easier to use than the pliers described in the patent.

BRIEF DESCRIPTION OF THE DRAWING

FIG. 1 is a representation of an orthodontic appliance which includes brackets and tubes adhesively bonded to the lingual side of the teeth; and FIG. 2 is a side view of a tool constructed in accordance with the concepts of the present invention, and which is intended to be used in the removal of orthodontic brackets and tubes which have been adhesively bonded to the lingual side of a patient's teeth.

DETAILED DESCRIPTION OF THE ILLUSTRATED EMBODIMENT

The orthodontic appliance shown in FIG. 1 includes, for example, a number of brackets 30 which are adhesively bonded to the anterior teeth of a patient, and a number of tubes 32 and 34 which are adhesively bonded to the lingual surfaces of the patient's posterior teeth. An arch wire 36 intercouples the brackets and tubes to complete the orthodontic appliance.

The tool of the present invention, as mentioned above, is shown in FIG. 2, and this tool is particularly adapted for removing the adhesively attached brackets 30 and tubes 32 and 34 from the lingual surfaces of the teeth after the orthodontic treatment has been completed.

The tool shown in FIG. 2 includes a first member made up of a handle 12 and a head 18, and a second member made up of a handle 14 and a head 22. The first member is pivoted to a bracket 10 by means of a pivot pin 10A, and the second member is pivoted to the bracket 10 by means of a second pivot pin 10B. The pivot pins 10A and 10B are spaced from one another on bracket 10, so that the two members pivot about respective pivot axes which are spaced from one another.

A spring 16 engages handles 12 and 14 to bias the handles apart, and to bias the heads 18 and 22 together as shown in FIG. 2. A depending post 24 is mounted on head 22, and a depending spring-loaded elongated member 20 is mounted on head 18. The post 24 has a distal end shaped to be inserted incisally between the base of a bracket or tube and the surface of the tooth to which it is bonded when the pliers are inserted into the mouth of a patient, and the elongated member 20 is shaped to extend down over the lingual surface of the tooth and over a bracket or tube bonded to the lingual surface. The member 20 has a tip on its distal end which is shaped to extend under the lower edge of the lingual bracket or tube.

Then, when the handles 12 and 14 are squeezed together against the bias of spring 16, the post 24 is forced incisally between the base of the bonded bracket or tube and the tooth, and the tip of the elongated member 20 causes the bonded bracket or tube to be stripped upwardly and freed from the tooth. When the pressure is released, the spring 16 biases the handles to their illustrated position, and causes the heads 18 and 22 to assume their illustrated closed position.

The invention provides, therefore, a simple and sturdy tool, in the form of specially constructed pliers, which are easy to use, and which provide a convenient means for removing adhesively bonded orthodontic brackets and tubes from the lingual surfaces of a patient's teeth after the orthodontic treatment has been completed. The unique feature of the tool of the invention is that the bonded bracket or tube can be removed from the tooth with virtually no torque being applied to the tooth. This obviates any dislodging of the tooth during the removal of the bracket or bond which could result in pain to the patient.

It will be appreciated that while particular embodiments of the invention have been shown and described, modifications may be made, and it is intended in the following claims to cover all modifications which come within the true spirit and scope of the invention.

What is claimed is:

1. A tool for removing an adhesively bonded orthodontic bracket or tube from the lingual surface of a tooth which comprises: first and second members pivotally coupled to one another, said first and second members defining first and second handles and first and second heads for the tool; a depending post mounted on one of the heads in position to engage the top of a bonded bracket or tube to be forced between the bracket or tube and the tooth to which it is bonded; and an elongated depending catch member mounted on the other of the heads and having a tip at the distal end thereof in position to extend under the edge of the bracket or tube when the post engages the top of the bracket or tube as the handles are squeezed together.

2. The tool defined in claim 1, and which includes a spring interposed between said first and second handles for biasing the handles apart and the first and second jaws to a closed position.

3. The tool defined in claim 1, in which said post is mounted on said lower head, and the elongated depending portion is mounted on the upper head in overhanging relationship with said post so as to permit the catch member to extend down behind the tooth for removal of a bracket adhesively bonded to the lingual side of the tooth.

4. The tool defined in claim 1, and which includes a transverse support member, and in which said first and second members are pivotally coupled to said support member at transversely spaced pivot points for pivotal movement about spaced pivotal axes.

5. The tool defined in claim 1, in which said catch member is pivotally mounted to the other one of sid heads and is spring-loaded.

* * * * *